United States Patent
Machida

[19]

[11] Patent Number: 6,095,995
[45] Date of Patent: *Aug. 1, 2000

[54] INGROWN NAIL CORRECTING DEVICE

[76] Inventor: Eiichi Machida, Itopia 301, 1-8-30, Naka, Kunitachi-shi, Tokyo, Japan

[*] Notice: Under 35 U.S.C. 154(b), the term of this patent shall be extended for 375 days.

[21] Appl. No.: 08/598,687

[22] Filed: Feb. 8, 1996

[30] Foreign Application Priority Data

Feb. 8, 1995 [JP] Japan .................................. 7-043397

[51] Int. Cl.[7] ...................................................... A61F 5/00
[52] U.S. Cl. ............................................. 602/30; 602/31
[58] Field of Search ........................................ 602/30, 31

[56] References Cited

U.S. PATENT DOCUMENTS

| | | | |
|---|---|---|---|
| 4,601,283 | 7/1986 | Chikama | 600/151 |
| 4,944,727 | 7/1990 | McCoy | 600/151 X |
| 5,261,872 | 11/1993 | Goldenberg | 602/31 |

*Primary Examiner*—Richard J. Apley
*Assistant Examiner*—Kim M. Lee
*Attorney, Agent, or Firm*—Varndell & Varndell, PLLC

[57] ABSTRACT

The ingrown nail correcting device is to correct ingrown toenails by using a plate-like member made from a shape memorizing alloy or shape memorizing resin material. A plate-like member (10) formed from a shape memorizing alloy or shape memorizing resin material is preliminarily made to memorize a specified shape at a specified temperature. The plate-like member (10) is bent in accordance with the bent portions of an ingrown nail (12) of a big toe (11) at room temperature, and adhesively bonded to the surface of the ingrown nail (12) with the aid of an adhesive agent. The atmospheric temperature is elevated to the specified temperature, whereby the ingrown nail (12) is corrected by the restoring force of the plate-like member (10) directed toward the arrows.

4 Claims, 3 Drawing Sheets

FIG. 1
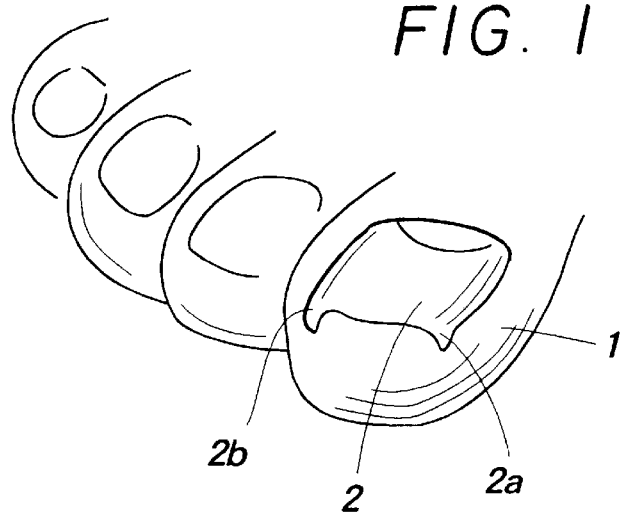
FIG. 2(a)
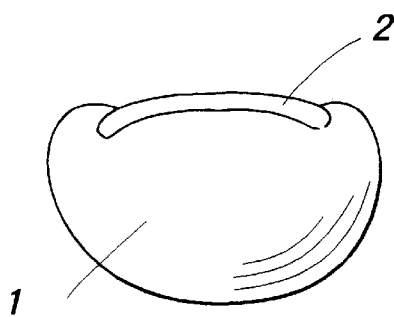
FIG. 2(b)
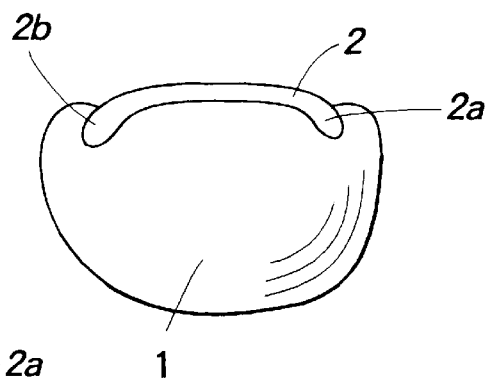
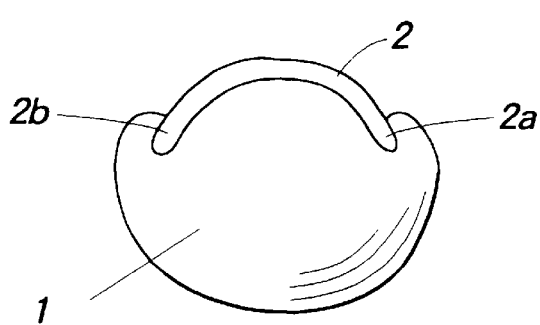
FIG. 2(c)

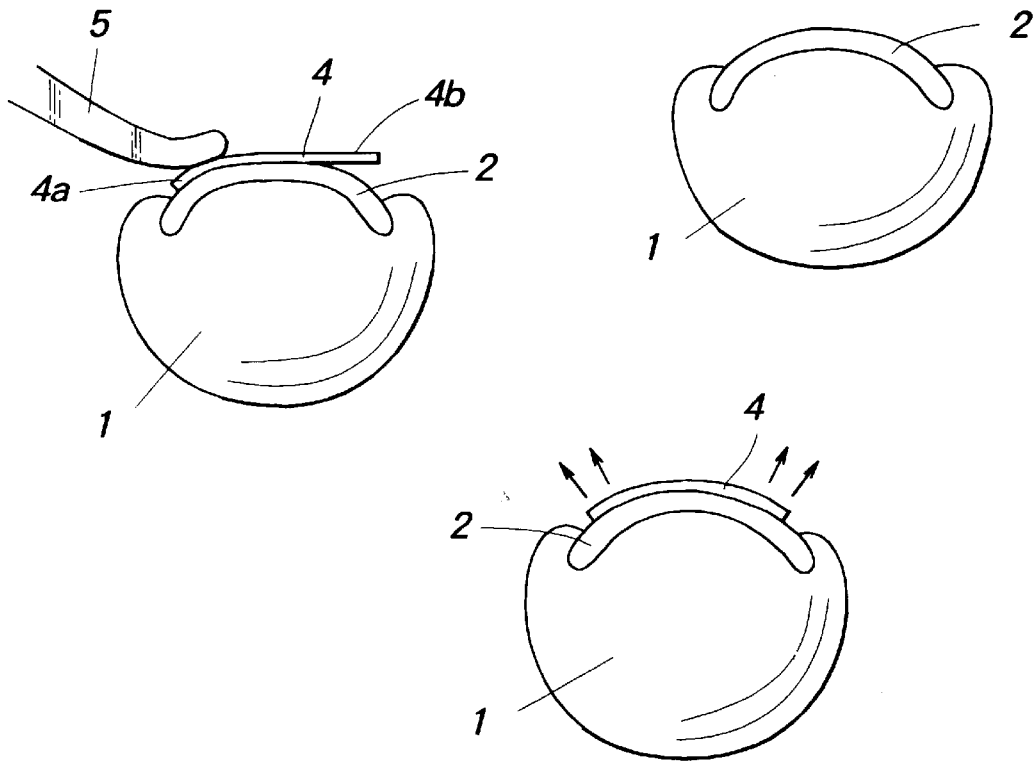
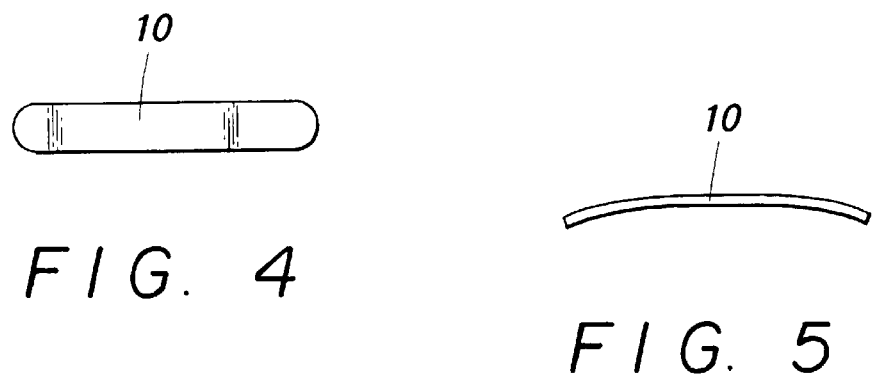

INGROWN NAIL CORRECTING DEVICE

BACKGROUND OF THE INVENTION

Field of the Invention

The present invention relates to an ingrown nail correcting device which is adhesively bonded to the surface of an ingrown nail to correct bent portions of the ingrown nail.

The ingrown toenail is a disease that side edges of the toenail shell are bent so as to warp inward and gnaw into the toenail groove or side toenail profile, such that soft tissues of the toe are pressured, causing a pain. The ingrown toenail occurs, in many cases, particularly at outer side edges 2a, 2b of a toenail shell 2 of a big toe 1 as shown in FIG. 1. Whereas a toenail shell 2 as shown in FIG. 2(a) is the normal toenail, a lightly ingrown toenail is as shown in FIG. 2(b) in which the outer side edges 2a, 2b of the toenail shell 2 are bent, and a heavily ingrown toenail is as shown in FIG. 2(c) in which the outer side edges 2a, 2b of the toenail shell 2 are bent to such a larger extent that the toenail groove or side toenail profile is mechanically pressured, where the big toe 1 is intensely pressed when shoes are put on, causing an awful pain to be generated.

The factors that cause the ingrown nail include congenital factors due to heredity and a posterior factors due to improper measures such as press by footwear, to-the-quick cut, and the like. In particular, when a cut to the quick or the like has resulted in an infection with bacteria, there are some cases where an abnormal granulation is formed, developing into an profile onychia accompanied by a heavy pain.

One medical treatment for the ingrown nail is to remove the ingrown portion by a surgical operation. However, this operation is rather complicated and has disadvantages in that the operation causes the toenail shell to be narrowed in width, and that the operation is impossible to execute when a bacteria infection has been involved.

As a treatment without the aid of operations, a flat, rectangular plate-like member 4 having a length generally equal to the width of the toenail shell 2 is made from a material such as metal or synthetic resin, as shown in FIG. 3, and a strong bio-adhesive agent is applied to the rear side of the plate-like member 4. First, as shown in FIG. 3(a), the plate-like member 4 is placed on the surface of the toenail shell 2, and bonded at its central portion. Next, as shown in FIG. 3(b), one edge 4a of the plate-like member 4, while being held by a metal bar 5, is adhesively bonded, and pressed until the adhesive agent is dried. Then, the plate-like member 4 is bonded to the other edge 4b over the entire width of the toenail shell 2. If the toenail is left in such a state, restoring force acts in the directions of arrows in FIG. 3(c) by the rigidity of the metal material or synthetic resin material, so that the bent portions of the ingrown toenail will be corrected so as to become flat, gradually.

However, with the use of the prior-art plate-like member 4 of a metal material or synthetic resin material as described above, the restoring force for correcting the ingrown toenail is indeed effective within the range of distortion of the metal material or synthetic resin material enabled by its elastic deformation, but decreases gradually due to a creeping phenomenon or the like beyond the range of distortion. Also, in order to retain enough rigidity to correct the ingrown nail, there arises a need of increasing the thickness of the plate-like member 4, where thickening the plate-like member 4 would conversely cause the adhesive agent to lack in strength such that the plate-like member 4 would be peeled off, disadvantageously. Thus, as a current situation, the aforementioned plate-like member 4 is not widely used.

SUMMARY OF THE INVENTION

The object of the present invention is therefore to provide an ingrown nail correcting device for solving the above problems and for conveniently treating ingrown toenails by using a shape memorizing alloy or shape memorizing resin material.

In order to achieve the above object, the present invention provides an ingrown nail correcting device comprising an elongated plate-like member which is made of a shape memorizing alloy or shape memorizing resin material and which will curve along a surface shape of a toenail shell at room temperature, and deform into a memorized shape when heated, wherein the ingrown nail correcting device is adhesively bonded to the surface of the toenail shell with an adhesive agent.

In use of the ingrown nail correcting device having the above constitution, the plate-like member that memorizes a specified shape at a specified temperature is adhesively bonded to the surface of an ingrown toenail by using an adhesive agent. By elevating the atmospheric temperature to the specified temperature with heating means, the ingrown toenail is corrected by a restoring force with which the plate-like member returns to the specified memorized shape.

BRIEF DESCRIPTION OF THE DRAWINGS

FIG. 1 is a perspective view of a toenail;

FIGS. 2(a), 2(b) and 2(c) are explanatory views of an ingrown toenail;

FIGS. 3(a), 3(b) and 3(c) are explanatory views of a prior art example.

FIG. 4 is a plan view of an embodiment;

FIG. 5 is a side view;

DETAILED DESCRIPTION OF THE PREFERRED EMBODIMENTS

The present invention is now described in detail based on an embodiment as illustrated in FIGS. 4 through 8.

FIG. 4 is a plan view of a plate-like member 10 made from a shape memorizing alloy or shape memorizing resin material, and formed into, for example, a 15 mm long, 3 mm wide, 0.2 mm thick generally rectangular shape. This plate-like member 10 is bent into a bowed shape in accordance with the surface shape of the toenail shell at room temperature, as shown in FIG. 5, but has memorized such a shape that it will flatten or inversely warp when heated.

Figure 6:
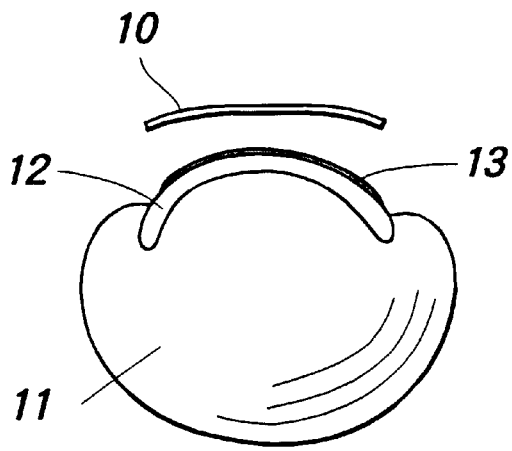
FIG. 6 is an explanatory view of a state in which the plate-like member is bonded to the ingrown toenail.
Figure 7:
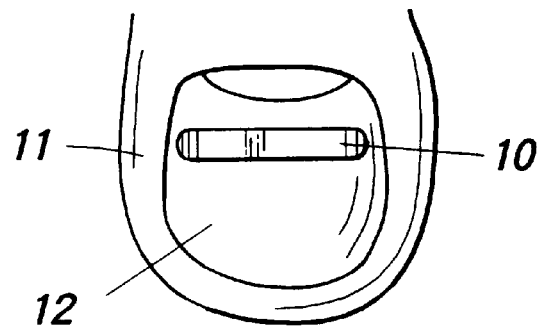
FIG. 7 is a plan view of the bonded state.

In actual use, as shown in FIGS. 6 and 7, the plate-like member 10 is adhesively bonded to the surface of an ingrown toenail 12 of a big toe 11 by using an adhesive agent 13 so that no clearances will be generated. Then, the whole is lightly pressed from above, and held as it is until the plate-like member 10 is completely bonded with the adhesive agent 13 dried.

In such a state, when the toenail under treatment is heated to the specified temperature at which the specified shape has previously been memorized, by warm air blows with a drier, or by warm water during a bath, the shape memorizing alloy or shape memorizing resin material will recover its memory so that it will restore the specified flat or warped-back shape.

Figure 8:
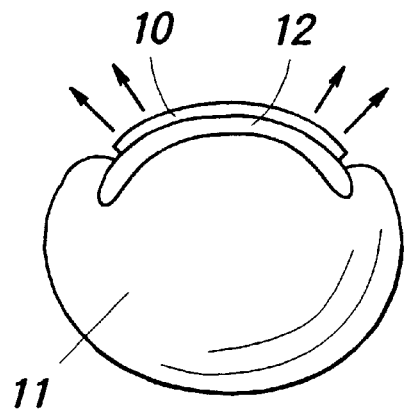
FIG. 8 is an explanatory view of the ingrown toenail under correction.

Accordingly, as shown in FIG. 8, the plate-like member 10 generates a force of restoration toward the directions of arrows, where the ingrown toenail 12 is pulled up particularly at its edge portions so that it will warp back oppositely to the bent shape. By implementing such a force-active state for a specified time period or by repeatedly implementing this state, the bent portions of the ingrown toenail 12 will be corrected gradually.

In this way, by using the plate-like member 10 of a shape memorizing alloy or shape memorizing resin material, the ingrown toenail 12 can be corrected with great simplicity. Also, by virtue of an extremely small quantity of the shape memorizing alloy or shape memorizing resin material required for use as the plate-like member 10 allows the correcting device to be low priced, while the patient himself or herself can correct the disease without needing a medical specialist. In addition, the adhesive bond of the plate-like member 10 can be peeled off with a peeling agent.

As described above, the ingrown nail correcting device according to the present invention, which uses a plate-like member composed of a shape memorizing alloy or shape memorizing resin material to correct the ingrown toenail, allows the plate-like member to be easily bent in accordance with the shape of the ingrown toenail. As a result, the ingrown nail correcting device is easy to handle and able to be adhesively bonded to the bent portions correctly and firmly. Further, the patient himself or herself is enabled to correct the ingrown toenail safely and simply, taking advantage of the restoring force of the plate-like member which is implemented by a simple operation of elevating the temperature.

What is claimed is:

1. An ingrown nail correcting device comprising an elongated plate member adhesively bonded to a surface of a nail shell with an adhesive agent, said plate member having a curved shape bent to match a curvature of said nail shell at room temperature, and said plate member is made of a material having said curved shape at room temperature and deforming to a memorized flat shape when heated above room temperature.

2. The ingrown nail correcting device according to claim 1, wherein the elongated plate member is made of a shape memorizing alloy.

3. The ingrown nail correcting device according to claim 1, wherein said elongated plate member is a shape memorizing resin material.

4. The ingrown nail correcting device according to claim 1, wherein said elongated plate member has a length of 15 mm, a width of 3 mm, and a thickness of 0.2 mm.

* * * * *